United States Patent
Watanabe et al.

(10) Patent No.: US 10,383,739 B2
(45) Date of Patent: Aug. 20, 2019

(54) ORTHOPAEDIC IMPLANT WITH DYNAMIC TRANS-FIXATION SLOT

(71) Applicant: SMITH & NEPHEW, INC., Memphis, TN (US)

(72) Inventors: Kohsuke Watanabe, Memphis, TN (US); Paul Tornetta, Chestnut Hill, MA (US)

(73) Assignee: SMITH & NEPHEW, INC., Memphis, TN (US)

(*) Notice: Subject to any disclaimer, the term of this patent is extended or adjusted under 35 U.S.C. 154(b) by 290 days.

(21) Appl. No.: 14/361,404

(22) PCT Filed: Nov. 30, 2012

(86) PCT No.: PCT/US2012/067185
§ 371 (c)(1),
(2) Date: May 29, 2014

(87) PCT Pub. No.: WO2013/082354
PCT Pub. Date: Jun. 6, 2013

(65) Prior Publication Data
US 2015/0142125 A1    May 21, 2015

Related U.S. Application Data

(60) Provisional application No. 61/565,452, filed on Nov. 30, 2011.

(51) Int. Cl.
| | | |
|---|---|---|
| *A61B 17/58* | (2006.01) | |
| *A61F 2/30* | (2006.01) | |
| *A61F 2/42* | (2006.01) | |
| *A61B 17/72* | (2006.01) | |
| *A61B 17/86* | (2006.01) | |
| *A61F 2/28* | (2006.01) | |

(52) U.S. Cl.
CPC .......... *A61F 2/4261* (2013.01); *A61B 17/725* (2013.01); *A61B 17/7233* (2013.01);
(Continued)

(58) Field of Classification Search
CPC ..... A61B 17/72; A61B 17/68; A61B 17/1725; A61B 17/7241; A61B 17/7291;
(Continued)

(56) References Cited

U.S. PATENT DOCUMENTS 4,776,330 A * 10/1988 Chapman ............... A61B 17/72
606/64
5,935,127 A * 8/1999 Border ............... A61B 17/1721
606/281

(Continued)

FOREIGN PATENT DOCUMENTS

| CA | 2526384 A1 | 9/2005 | |
| EP | 1992299 A2 * | 11/2008 | ......... A61B 17/7233 |
| EP | 1992299 A3 | 3/2009 | |

OTHER PUBLICATIONS

Authorized officer In Ho Han, International Search Report/Written Opinion in PCT/US2012/067185 dated Mar. 19 2013, 11 pages.
(Continued)

*Primary Examiner* — Ann Schillinger

(57) ABSTRACT

An orthopaedic implant for use with a fastener having at least one of threads and grooves includes a body defining a long axis. The body includes an inner wall defining an elongated slot. The inner wall includes a pair of opposing walls and a single projection disposed on the inner wall. When the fastener is inserted into the slot, the single projection slidably fits within a groove of the fastener to limit sliding of the implant over the fastener along an axis substantially transverse to the long axis and to permit sliding of the implant over the fastener along the long axis.

27 Claims, 13 Drawing Sheets

(52) U.S. Cl.
CPC ...... *A61B 17/7241* (2013.01); *A61B 17/8625* (2013.01); *A61B 17/8685* (2013.01); *A61F 2/28* (2013.01)

(58) Field of Classification Search
CPC ............ A61B 17/8605; A61B 17/8625; A61B 2017/564; A61B 17/725; A61B 17/744; A61B 17/7233; A61B 17/7225; A61B 17/864; A61B 17/8057; A61B 17/8061; A61B 17/86
See application file for complete search history.

(56) References Cited

U.S. PATENT DOCUMENTS

| | | | |
|---|---|---|---|
| 6,296,645 | B1* | 10/2001 | Hover .................... A61B 17/72 606/62 |
| 2002/0151898 | A1 | 10/2002 | Sohngen et al. |
| 2005/0010223 | A1 | 1/2005 | Gotfried |
| 2008/0183171 | A1 | 7/2008 | Elghazaly |
| 2008/0249580 | A1 | 10/2008 | Evans |
| 2011/0009866 | A1 | 1/2011 | Johnson et al. |
| 2011/0160729 | A1* | 6/2011 | Overes ................ A61B 17/7241 606/64 |
| 2011/0196370 | A1* | 8/2011 | Mikhail ............... A61B 17/744 606/62 |

OTHER PUBLICATIONS

Extended European Search Report for European Application No. 12853889.9, dated Jul. 23, 2015.

Examination Report issued in Canadian Application No. 2,857,494 dated Oct. 15, 2018.

* cited by examiner

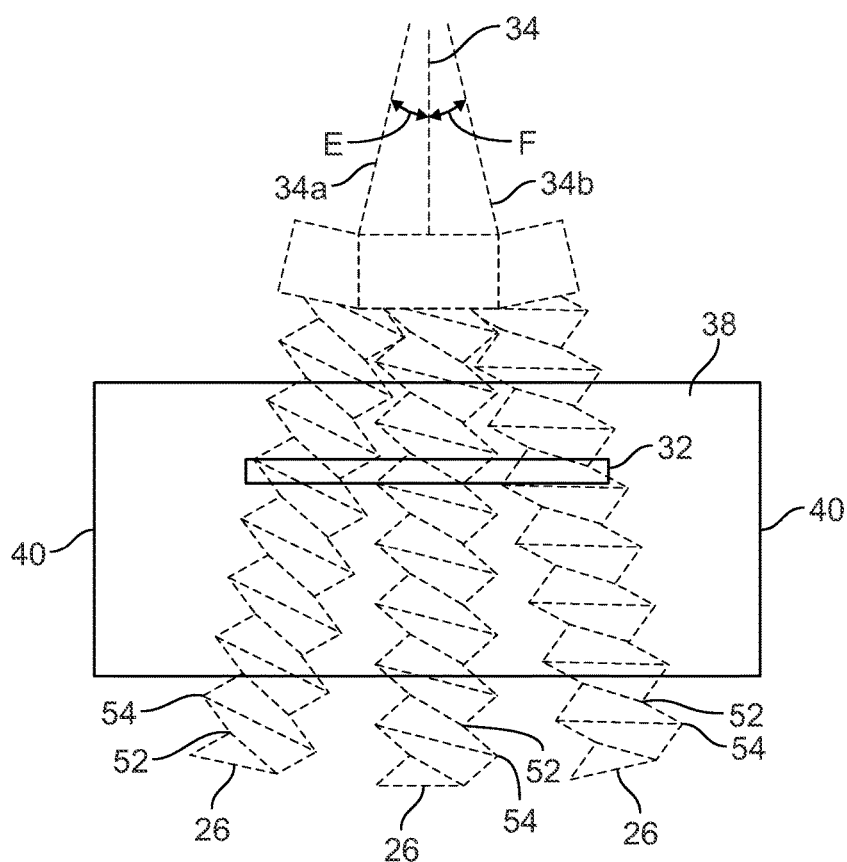
FIG. 4K
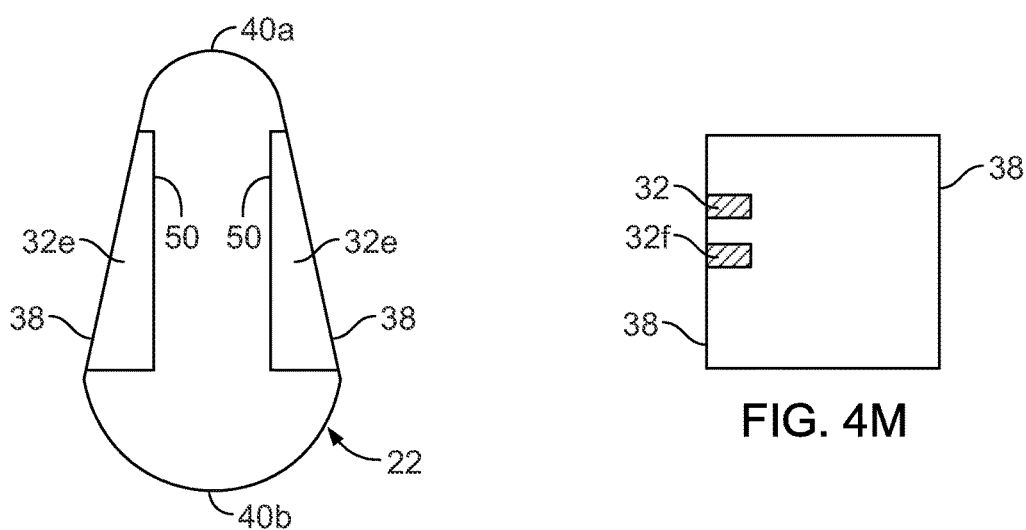
FIG. 4L
FIG. 4M

ORTHOPAEDIC IMPLANT WITH DYNAMIC TRANS-FIXATION SLOT

CROSS-REFERENCE TO RELATED APPLICATIONS

This application claims priority to and the full benefit of U.S. Provisional Application Ser. No. 61/565,452, filed Nov. 30, 2011 and entitled "ORTHOPAEDIC IMPLANT WITH DYNAMIC TRANS-FIXATION SLOT," the entire contents of which are incorporated herein by reference.

FIELD

This document relates to a system for coupling bone portions across a fracture and, more specifically, to an orthopaedic implant used to treat fractures of bones such as the femur, humerus, and tibia.

BACKGROUND

There are a variety of devices used to treat fractures of bones, such as the femur, humerus, and tibia. For example, fractures of the femur have been successfully treated with an orthopaedic implant, such as an intramedullary nail longitudinally placed within the medullary canal to connect the bone fragments. Such implants typically include a plurality of openings, such as circular holes and elongated slots, which receive fasteners to attach the implant to the cortical surface of the bone. While circular holes prevent the fasteners from translating in the axis of the nail, elongated slots can allow the fasteners to slide, translate, or dynamize, with respect to the axis of the nail. Some holes are threaded to prevent the nail from sliding or translating over or along the axis of the fastener. "Dynamization" refers to a movement of the fastener and the nail relative to each other in a direction generally parallel to the axis of the nail. Such dynamization can promote healing of the bone by putting the fracture site under stress.

Due to the fact that slots in the nail commonly have no threads in order to accommodate dynamization, the nail can also translate along the axis of the fastener in cases where either there are no threaded holes near the slots or the surgeon chooses not to insert fasteners into the threaded holes near the slots. Such translation of the nail along the axis of the fastener can be referred to as the "windshield wiper effect," which is undesirable and can lead to bone instability. What is needed is an orthopaedic implant system that will prevent, for example, the intramedullary nail from translating in the axis of the fastener while still allowing the fastener to dynamize in or along the axis of the nail. "Trans-fixation" refers to an implant that can dynamize over the fastener relative to one axis while being fixated to the fastener relative another axis.

Prior attempts have tried to use threaded slots with threaded sidewalls that engage the threads of the fastener such that the fastener can be displaced and locked within the slot for intraoperative fracture compression purpose. However, such approaches do not allow the implant, for example the nail, to dynamize once the fastener is locked in the threaded slot. Furthermore, due to the engagement of the threads of the fastener and those of the slot, dynamization of the nail in this situation will rotate the fastener on its axis, resulting in the fastener screwing in and out of the bone. This is undesirable as it causes severe pain in patients. Other disadvantages of prior attempts include that they require the threads of the slot to precisely or substantially conform to the threads of the fastener, thus limiting the types of fasteners that can be inserted into the threaded slot. Additionally, the fastener generally needs to be inserted into the threaded slot at a precise angular orientation in order for the threads of the slot and the threads of the fastener to engage each other properly.

SUMMARY

According to one aspect, an orthopaedic implant for use with a fastener having at least one of threads and grooves includes a body defining a long axis. The body includes an inner wall defining a slot, generally an elongated slot. The inner wall includes a pair of opposing walls and a single projection disposed on the inner wall. The inner wall may include a pair of non-parallel opposing walls in other embodiments. When the fastener is inserted into the slot, the single projection slidably fits within a groove of the fastener to limit sliding of the implant over the fastener along an axis substantially transverse to the long axis and to permit sliding of the implant over the fastener along the long axis.

Implementations of this aspect may include one or more of the following features.

For example, the pair of opposing walls may run substantially parallel to the long axis. The single projection disposed on the inner wall may comprise a leading edge running substantially parallel to the long axis. A second projection may be disposed on the inner wall. The inner wall may comprise a leading edge running substantially parallel to the long axis. A second single projection may be disposed on the inner wall. The second single projection may have a leading edge running substantially parallel to the long axis. The second single projection may be positioned generally opposite the single projection. The second single projection may be positioned generally adjacent and parallel to the single projection and separate or disconnected from the single projection. The inner wall may further define a semi-cylindrical portion of the slot. The semi-cylindrical portion of the slot may comprise an arc not greater than approximately 180 degrees. A projection may be disposed on the semi-cylindrical portion. The projection may be configured to engagingly fit within a groove of the fastener when the fastener is positioned proximate the projection disposed on the semi-cylindrical portion. The projection disposed on the semi-cylindrical portion may form a continuous surface with the single projection disposed on the inner wall. The continuous surface may run circumferentially around the inner wall of the slot. The continuous surface may not be parallel to the long axis. One or more additional projections may be positioned on the inner wall such that the single projection and the one or more additional projections are aligned substantially parallel to the long axis. The one or more additional projections and the single projection may be disconnected such that a continuous surface is not defined between them. The pair of opposing walls may be parallel to each other and spaced apart from each other a distance substantially corresponding to an outer diameter of the fastener. The single projection may be retractably disposed in an opening defined in the inner wall such that a portion of the single projection extends into the slot through the opening. The single projection may be spring loaded. The portion of the single projection extending into the slot may be lockably varied. The single projection may extend into the slot along an axis that is substantially parallel to the long axis or substantially orthogonal to the long axis.

According to another aspect, a method of treating a bone fracture includes inserting an orthopaedic implant into a canal of a fractured bone, inserting a first fastener through the hole, and inserting a second fastener transversely through the slot of the implant. The implant has a body defining a long axis. An inner wall defines a hole and an elongated slot. The implant is free to slide over the second fastener substantially along the long axis by interaction with a single projection or multiple parallel and separate (not connected) projections disposed on the inner wall defining the slot. The projection has a leading edge running substantially parallel to the long axis. A first part of the fractured bone connected to the first fastener can move along the long axis in relation to a second part of the fractured bone connected to the second fastener.

According to yet another aspect, orthopaedic implant for use with a fastener having a protrusion includes a body defining a long axis. The body includes an inner wall defining a slot. The inner wall includes a pair opposing walls, and a channel defined in the inner wall. When the fastener is inserted into the slot, the protrusion of the fastener slidably fits within the channel to limit sliding of the implant over the fastener along an axis substantially transverse to the long axis. The implant is free to slide over the fastener substantially along the long axis by interaction with the channel.

Implementations of this aspect may include one or more of the following features.

For example, the channel may be disposed on one of the pair of opposing walls. The inner wall may further define a semi-cylindrical portion of the slot. At least a portion of the channel may be formed within the semi-cylindrical portion of the slot.

According to a further aspect, an orthopaedic implant for use with a fastener having at least one of threads and grooves includes a body defining a first long axis and an insert member defining a long axis. The body includes a slot with parallel or non-parallel walls. The insert member includes a pair of opposing outer walls and a pair of opposing inner walls running substantially parallel to the second long axis, and a projection or multiple parallel and separate (not connected) projections disposed on an inner wall of the insert member. The parallel inner walls of the insert are spaced apart from each other a distance substantially corresponding to an outer diameter of the fastener. The projection has a leading edge(s) running substantially parallel to the second long axis. The insert member can be inserted into the slot so that the second long axis is generally aligned or parallel with the first long axis, such that, when the fastener is inserted into the insert member, the projection slidably fits within a groove of the fastener to limit sliding of the implant over the fastener along an axis substantially transverse to the second long axis. The implant is free to slide over the fastener along the second long axis by interaction with the projection.

According to another further aspect, an orthopaedic implant for use with a fastener having a protrusion includes a body defining a first long axis and an insert member defining a second long axis. The body includes a slot with parallel or non-parallel walls. The insert member includes a pair of opposing outer walls and a pair of opposing inner walls running substantially parallel to the second long axis, and a channel formed on an inner wall of the insert member. The opposing inner walls of the insert are spaced apart from each other a distance substantially corresponding to an outer diameter of the fastener. The insert member can be inserted into the slot so that the second long axis is generally aligned or parallel with the first long axis, such that, when the fastener is inserted into the slot, a protrusion of the fastener slidably fits within the channel to limit sliding of the implant over the fastener along an axis substantially transverse to the second long axis. The implant is free to slide over the fastener along the second long axis by interaction with the channel.

According to yet another further aspect, an orthopaedic implant for use with a fastener having at least one of threads and grooves includes a body defining a long axis. The body includes an inner wall defining an elongated slot. The inner wall includes a pair of opposing walls running substantially parallel to the long axis and a projection disposed on the inner wall. When the fastener is inserted into the slot, the projection slidably fits within a groove of the fastener and establishes a point of contact with the fastener. The projection is configured to limit sliding of the implant over the fastener along an axis substantially transverse to the long axis and to permit sliding of the implant over the fastener along the axis. As the implant slides over the fastener along the long axis, the point of contact with the fastener remains substantially the same.

Implementations of this aspect may include one or more of the following features.

For example, the sliding of the implant over the fastener along the long axis may not cause the fastener to rotate. When the fastener is at its final target depth within the implant, the implant may slide over the fastener along the long axis.

The details of one or more implementations are set forth in the accompanying drawings and the description below. Other features, aspects, and advantages will become apparent from the description, the drawings, and the claims.

BRIEF DESCRIPTION OF THE DRAWINGS

FIGS. 4A-4M are top and cross-sectional views of alternatives of the raised edge within the slot.

DETAILED DESCRIPTION

Figure 1A:
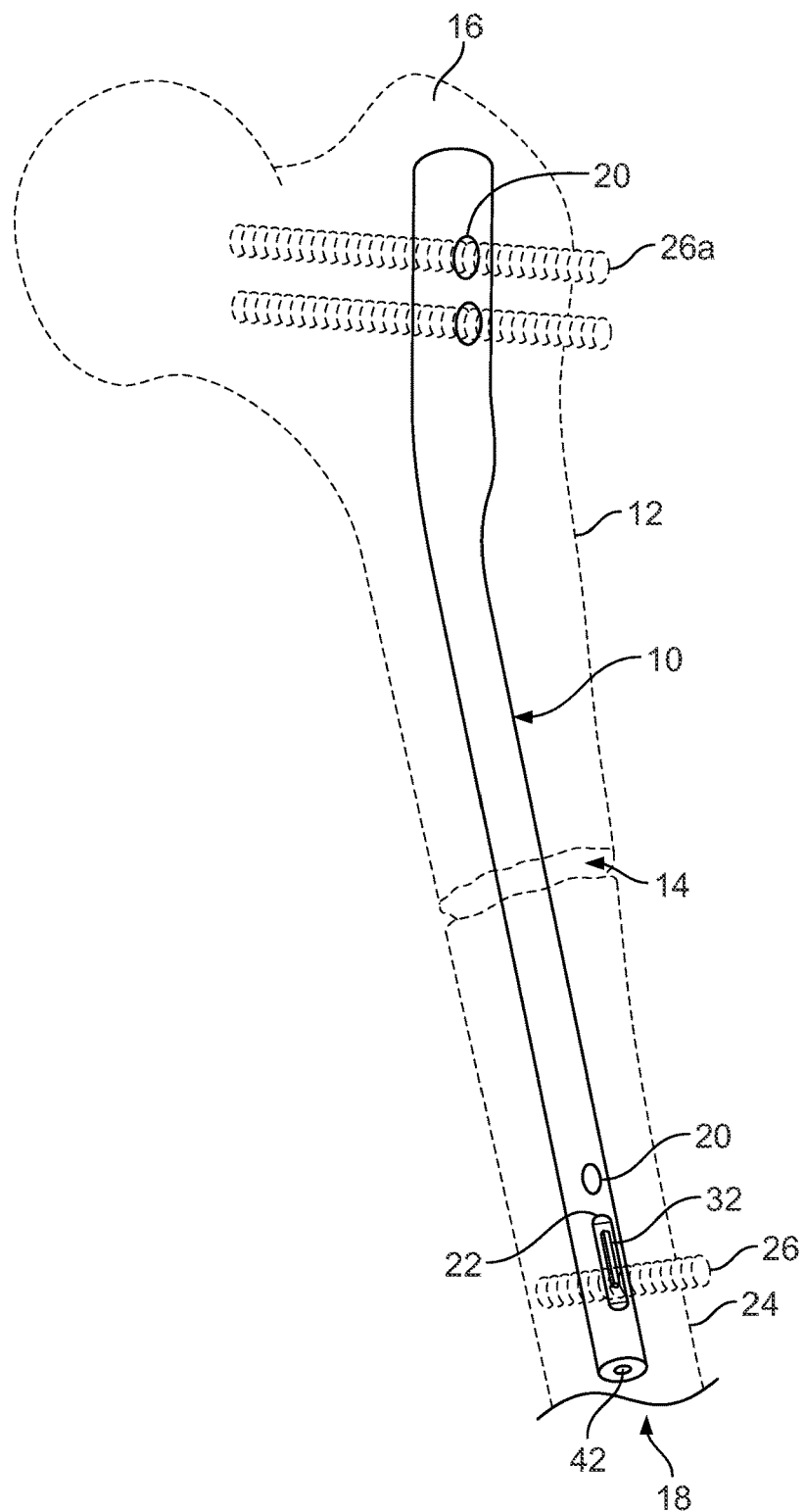
FIG. 1A is a perspective view of an orthopaedic implant with a raised projection or edge within a slot.
Figure 1B:
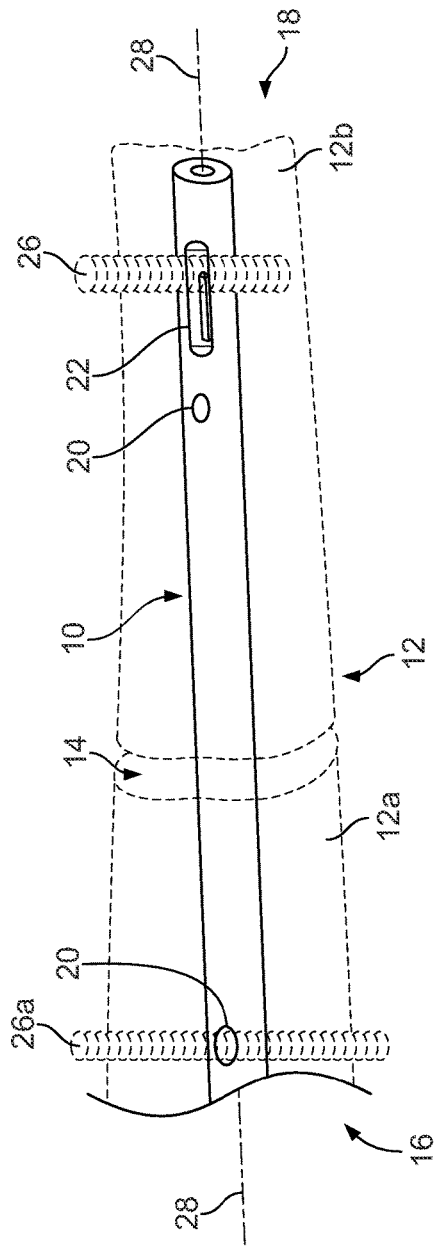
FIGS. 1B-1C illustrate dynamization of bone pieces using the orthopaedic implant with a raised edge within a slot.
Figure 1C:
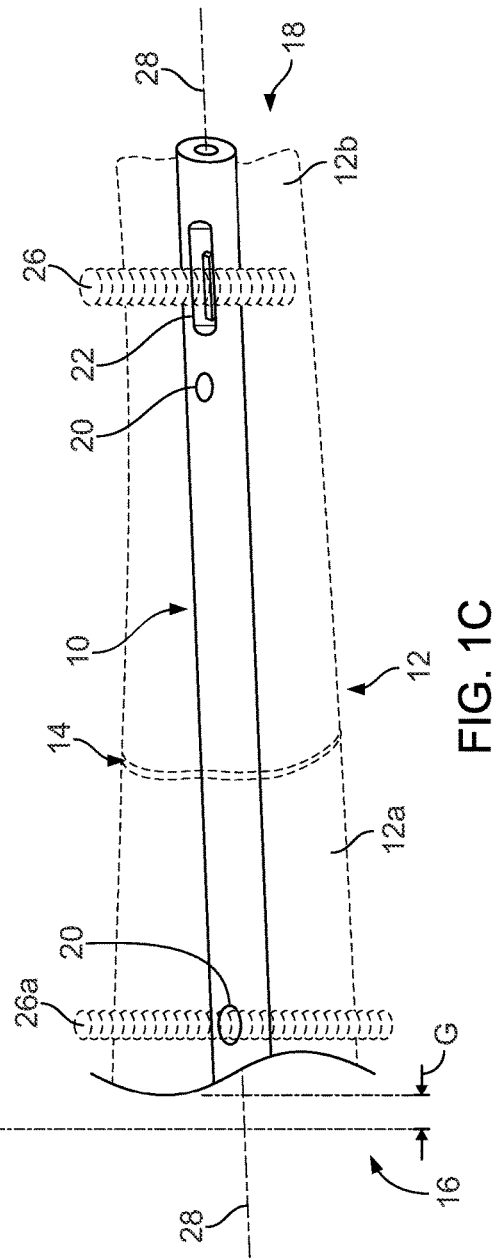
Figure 2:
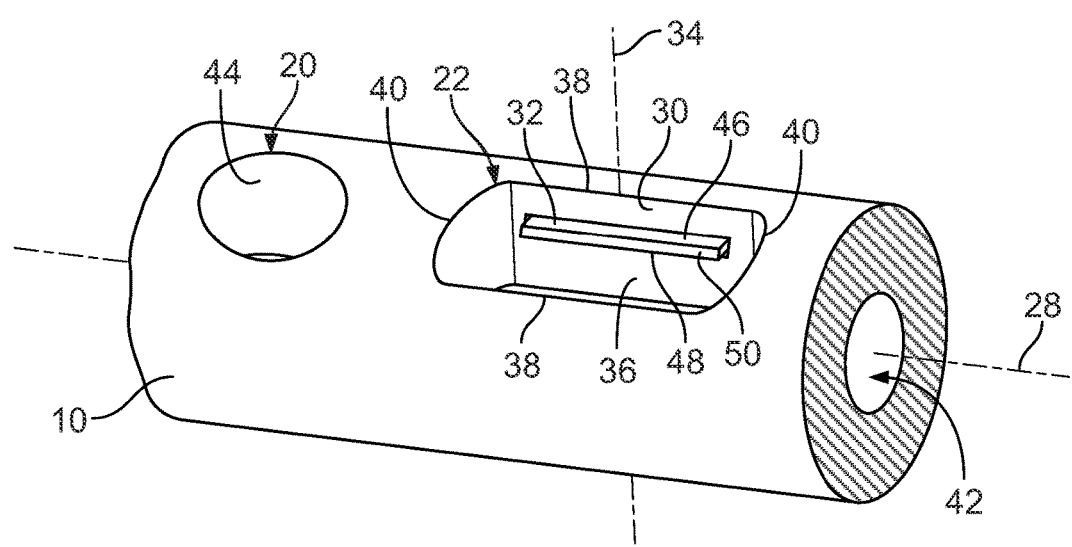
FIG. 2 is a sectional perspective view of the orthopaedic implant with a raised edge within a slot.

Referring to FIGS. 1-2, to treat fractures of bones, a surgeon may place an orthopaedic implant, such as an intramedullary nail 10, into a canal of a fractured bone, such as a femur 12, to repair, for example, a fracture site 14. The intramedullary nail 10 has a proximal end 16 and a distal end 18 and can have a plurality of transverse openings, such as circular openings 20 and elongated slot 22, positioned along its length. In use, the nail 10 is secured to a cortical layer of bone 24 using one or more fasteners 26, 26a that are inserted into appropriate circular openings 20 and/or slots 22. The fastener 26 can include screw or helical threads along all or portions of its length. The threads of the fastener 26 can be in the form of protrusions that act like threads. The circular opening 20 prevents translation of the intramedullary nail 10 over the inserted fastener 26 in a direction generally parallel to a longitudinal axis 28 (FIG. 2) of the nail 10 while the elongated slot 22 allows the intramedullary nail 10 to translate over the fastener 26 axially in a direction generally parallel to the longitudinal axis 28.

The nail 10 includes one or more elongated slots 22 that are defined by a circumferential inner wall 30. The slot 22 is elongated generally in the direction of the longitudinal axis 28 and includes a center portion 36 having two substantially opposing sidewalls 38. The opposing side walls 38 can be parallel to each other. The inner wall 30 can further define a semi-cylindrical portion 40 at a proximal and/or a distal end of the center portion 36. The inner wall 30 of the slot 22 includes a projection, protrusion, blade, or raised edge 32 that engages with, for example, threads of the fastener 26 to prevent the inserted fastener 26 from sliding in a direction parallel to a transverse axis 34 of the intramedullary nail 10 while still allowing translation of the fastener 26 along the longitudinal axis 28. The transverse axis 34 is generally perpendicular to the longitudinal axis 28. The raised edge 32 can be positioned on one or both of the opposing sidewalls 38 and is generally parallel to the longitudinal axis 28. The raised edge 32 and the intramedullary nail 10 can be formed from a single piece of material, or the raised edge 32 can be formed separately from the nail 10, such as in the form of an insert, and later secured to the inner wall 30 by, for example, welding, press-fit, or other suitable attachment mechanism. The raised edge 32 and the intramedullary nail 10 can be formed from the same material or different material from that of the nail 10. The raised edge 32 and the intramedullary nail 10 can be formed from any biocompatible material or a combination of biocompatible materials, such as certain metal alloys and polymers, for example, shape-memory materials and PEEK. The raised edge 32 can be rigid, flexible, malleable, or deformable. Multiple raised edges 32 may be placed on same or opposed sidewalls 38 of the slot 22 as individual separate and parallel edges. In some cases, the intramedullary nail 10 includes a central cannulation 42 that can extend, for example, from the proximal end 16 to the distal end 18. A cylindrical wall 44 defines the circular opening 20 through the nail 10 and can be smooth or threaded.

In use, as illustrated in FIGS. 1B-1C, the intramedullary nail 10 can be inserted into the canal of a fractured bone, such as the femur 12, to repair the fracture site 14 while providing dynamization. For example, a first part of bone 12a can be secured to the nail 10 towards the proximal end 16 using a fastener 26a that is inserted transversely through the circular opening 20. A second part of bone 12b can be secured to the nail 10 towards the distal end 18 using a fastener 26 that is inserted transversely through the slot 22. As indicated by an arrow G, the first part of bone 12a can translate or dynamize relative to the second part of bone 12b in a direction generally parallel to the longitudinal axis 28 of the nail 10.

Figure 3A:
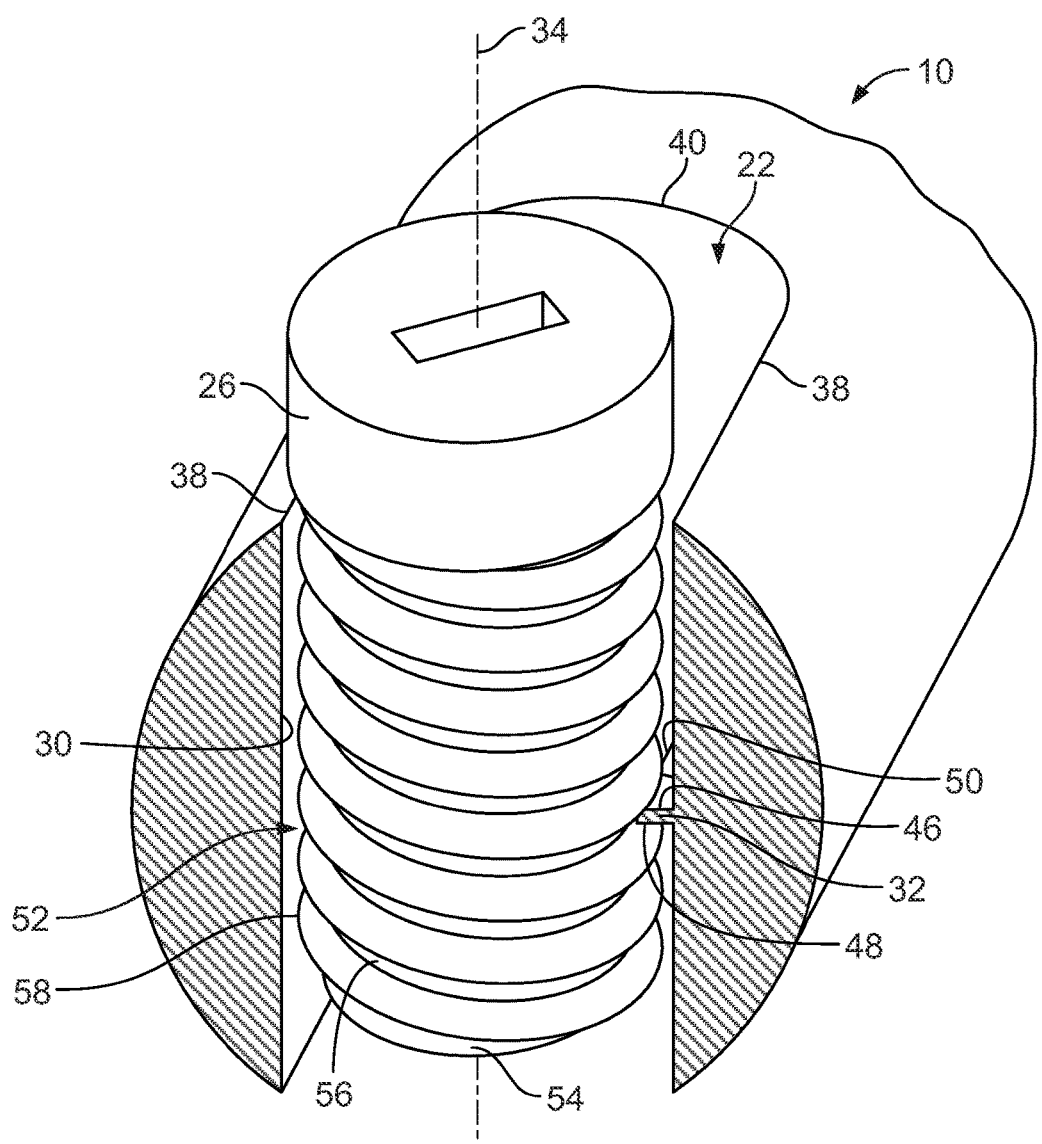
FIG. 3A is a perspective partial cross-sectional view of the orthopaedic implant with a raised edge within a slot and a fastener.
Figure 3B:
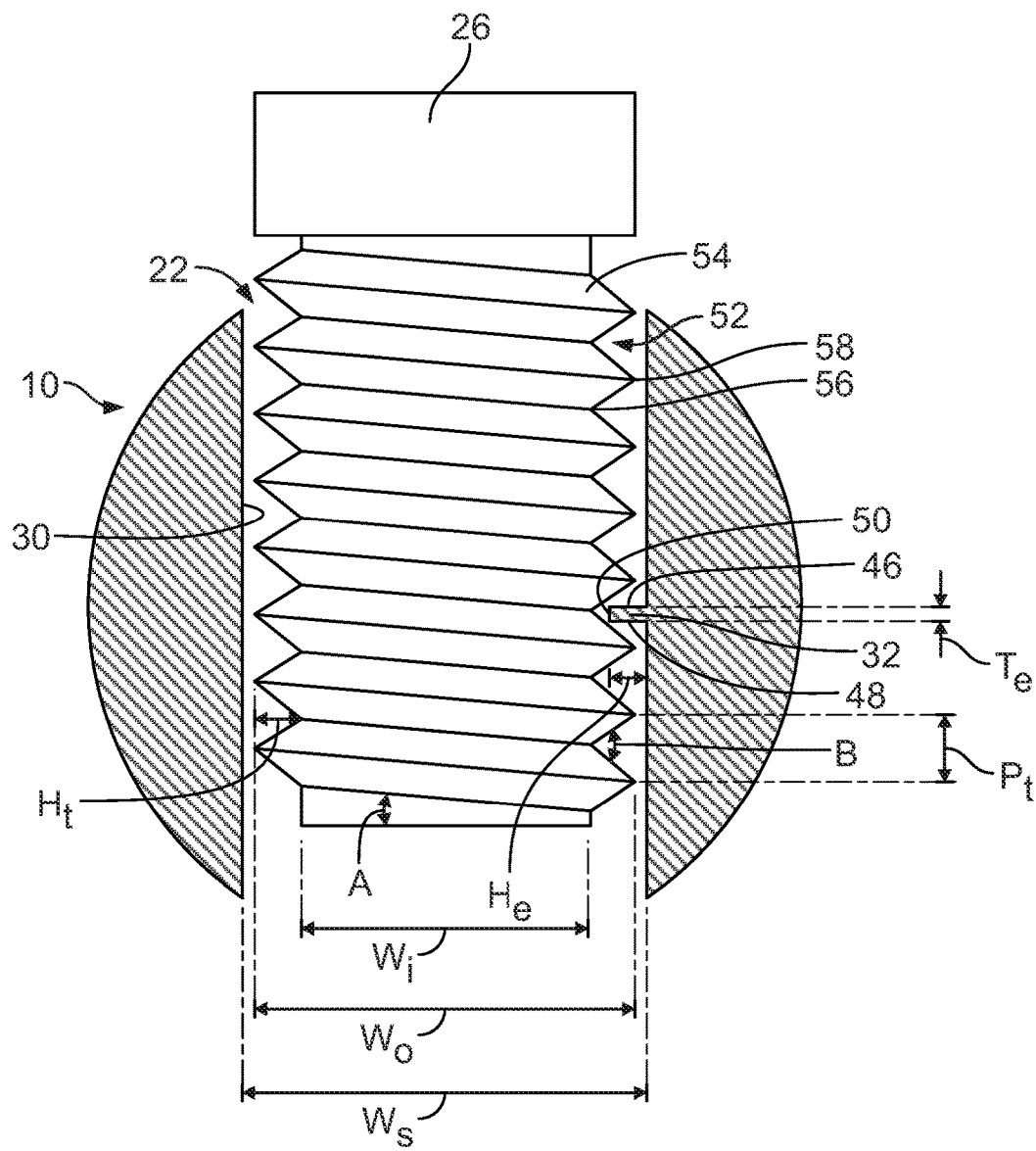
FIG. 3B is a partial cross-sectional view of the orthopaedic implant with a raised edge within a slot and a fastener.

Referring to FIGS. 3A-3B, the fastener 26 may slidably engage within the slot 22 by interaction with the raised edge 32 such that the fastener 26 can slide, or translate, along the longitudinal axis 28 (FIG. 2) while being prevented from sliding in a direction parallel to or along the transverse axis 34. The raised edge 32 can be positioned along the cirumferential inner wall 30 of the slot 22 as described further below.

The raised edge 32 includes a top surface 46, a bottom surface 48, and a leading edge 50. The top surface 46 and bottom surface 48 are generally flat and can be substantially parallel, converging, or diverging. The surfaces 46, 48 can also be roughened. The leading edge 50 can be a flat surface, a curved surface, or a sharp edge. In use, the fastener 26 is inserted into the slot 22 at a desired location by, for example, screwing the fastener 26 through the cortical layer of bone 24. The fastener 26 can be oriented such that it is parallel to the transverse axis 34 and perpendicular to the longitudinal axis 28. As the fastener 26 is inserted into the slot 22, for example by screwing, the leading edge 50 of the raised edge 32 and a portion of the top surface 46 and bottom surface 48 slidably engage a groove 52 of threads 54 such that the fastener 26 may translate along the longitudinal axis 28 while substantially being prevented from sliding along the transverse axis 34. Rotational motion of the fastener 26 about the transverse axis 34 may be unaffected by a presence of the raised edge 32 on the opposing sidewalls 38. While the fastener 26 is engaged with the raised edge 32, the leading edge 50 of the raised edge 32 may substantially come in contact with a portion of the groove 52, for example a bottom portion 56 of the groove 52. As the fastener 26 engaged within the slot 22 translates relative to the nail 10 in a direction generally parallel to the longitudinal axis 28, a point of contact with the fastener 26 that is established by the raised edge 32 within the groove 52 can remain substantially the same throughout the range of motion. In some cases, a portion of the inner wall 30 adjacent the fastener 26 substantially comes in contact with a top portion 58 of the thread 54.

In the example illustrated in FIGS. 3A-3B, only a single raised edge 32 is positioned on one of the opposing sidewalls 38. Consequently, fasteners having different thread configurations can be used as long as the single raised edge 32 can engage with a groove of the fastener.

Referring to FIG. 3B, the slot 22 has a width ($W_s$) that is approximately equal to or greater than an outer width ($W_o$) corresponding to an outer diameter of the fastener 26. The fastener 26 includes an inner width ($W_i$) corresponding to an inner diameter of the fastener 26, a helix angle (A), a thread angle (B), a thread pitch ($P_t$), and a thread height ($H_t$). The raised edge 32 has a thickness ($T_e$) and a height ($H_e$). The thickness ($T_e$) can vary along the height ($H_e$) of the raised edge 32 and is typically smaller than the thread pitch ($P_t$) of the threads 54. For the case when the width ($W_o$) of the fastener 26 is approximately equal to the width ($W_s$) of the slot 22, the height ($H_e$) of the raised edge 32 generally satisfies the following relationship:

$$H_e < (W_o - W_i)/2$$

For the case when the width ($W_o$) of the fastener 26 is less than the width ($W_s$) of the slot 22, the height ($H_e$) of the raised edge 32 generally satisfies the following relationship:

$$H_e > (W_s - W_o)/2$$

Dimensions of the raised edge 32 can be varied accordingly depending on specific geometries and positioning requirements of the fastener 26. For example, if the fastener 26 substantially comes in contact with only one of the parallel sidewalls 38, the height ($H_e$) of the raised edge 32 positioned opposite a wall-contacting side of the fastener 26 generally satisfies the following relationship:

$$W_s - W_o < H_e < W_s - [(W_o + W_i)/2]$$

Figure 4A:
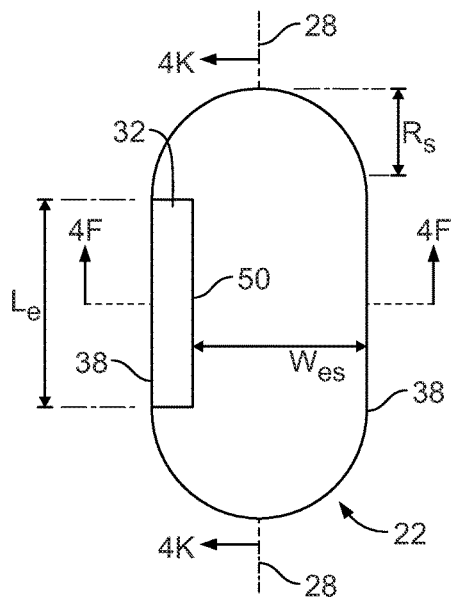

Referring to FIGS. 4A-4M, the configuration of raised edge 32 within the inner wall 30 can vary as required by a particular requirement of the orthopaedic implant 10. For example, the raised edge 32 can be positioned on one of the opposing sidewalls 38, as shown in FIG. 4A. In such a configuration, the length ($L_e$) of each raised edge 32 can be substantially equal to or less than a length of the opposing sidewall 38 measured in a direction generally parallel to the longitudinal axis 28 of the intramedullary nail 10. The intramedullary nail 10 can translate axially in a direction generally parallel to the longitudinal axis 28 over the fastener 26 but not transversely along the transverse axis 34 as long as a portion of the threads 54 engages a portion of the raised edge 32. To ensure continuous engagement between a portion of the threads 54 and a portion of the raised edge 32, a proximal and/or distal end of the raised edge 32 can be spaced apart from a proximal and/or distal end, respectively, of the slot 22 by a distance ($R_s$) that is less than the outer width ($W_o$) of the fastener 26, preferably, less than half of the outer width $W_o$ of the fastener 26. Width ($W_{es}$) between the leading edge 50 and the opposing sidewall 38 can be substantially equal to half of the sum of the outer width ($W_o$) and the inner width ($W_i$) of the fastener 26. FIG. 4F is a cross-sectional view taken along line 4F-4F in FIG. 4A.

Figure 4B:
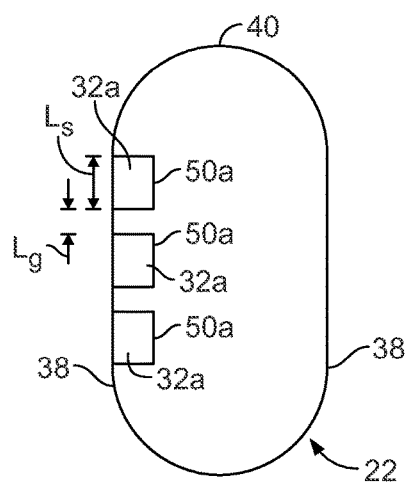
Figure 4C:
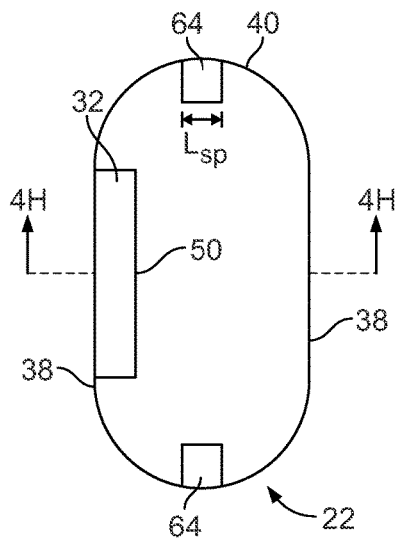

In another implementation, the raised edge 32 can be in the form of multiple segments, or raised edges 32a, as best seen in FIG. 4B. Each raised edge 32a can have a length ($L_s$). A gap between adjacent segments has a gap length ($L_g$) in a direction generally parallel to the longitudinal axis 28 of the intramedullary nail 10. The length ($L_s$) and the gap length ($L_g$) can vary for each raised edge 32a. Raised edges 32a can be arranged along an axis substantially parallel to the longitudinal axis 28.

In another implementation, the raised edge 32 can be accompanied by a short portion 64 having a length ($L_{sp}$) that can be positioned on the semi-cylindrical portion 40 of the slot 22 such that the short portion 64 is substantially parallel to the horizontal plane of the nail 10 and able to engage the proximate groove 52 of the inserted fastener 26 (not shown). A cross-sectional view taken along the line 4H-4H is shown in FIG. 4H.

Figure 4D:
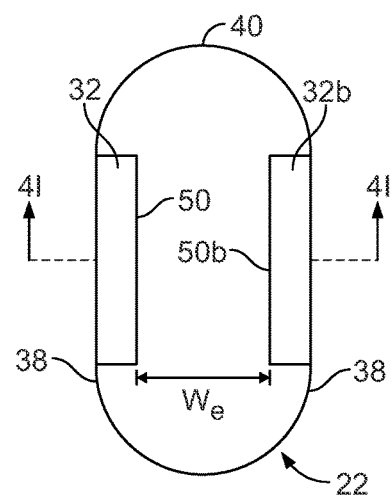

The raised edge 32 can be positioned on one of the opposing sidewalls 38, and another raised edge 32b can be positioned on the opposite side of the opposing sidewall 38, as seen in FIG. 4D. Raised edges 32, 32b that sequentially contact a groove 52 of the fastener 26 can be separated by an offset distance ($O_e$) in a direction generally parallel to the transverse axis 34 of the intramedullary nail 10. The offset distance ($O_e$) can be equal to approximately 50% of the thread pitch ($P_t$) of the fastener 26 to simultaneously and slidably engage the grooves 52 on opposite sides of the fastener 26. Alternatively, the offset distance ($O_e$) can be greater or less than 50% of the thread pitch ($P_t$) of the fastener 26. Width ($W_e$) between leading edges 50, 50b that face each other can be substantially equal to the inner width ($W_i$) of the fastener 26.

Figure 4E:
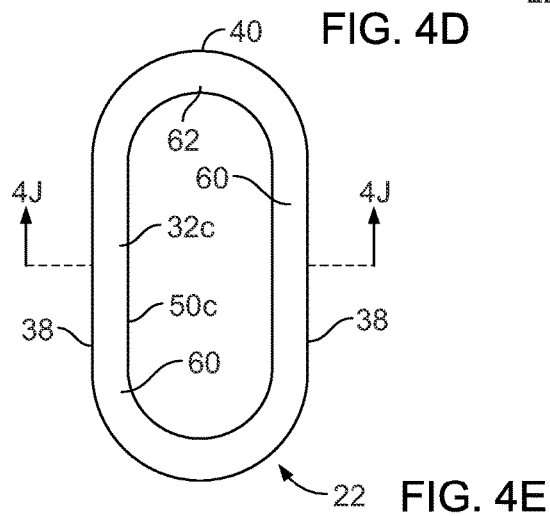
Figure 4F:
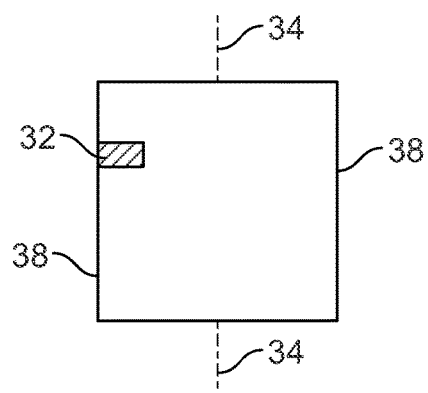

A raised edge 32c can run around a circumference of the inner wall 30 as best seen in FIG. 4E. The raised edge 32c can have a straight portion 60 positioned on the opposing sidewalls 38 of the slot 22 that generally runs parallel to the longitudinal axis 28. The raised edge 32c can have a curved portion 62 positioned, for example, on the semi-cylindrical portion 40 of the slot 22, that can be curved and generally follows a shape of a proximate groove 52 of the inserted fastener 26 (not shown). The curved portion 62 of the raised edge 32 can smoothly connect the opposing straight portions 60 of the raised edge 32 such that a continuous surface is defined.

Figure 4G:
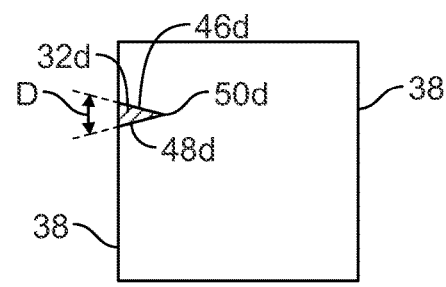
Figure 4H:
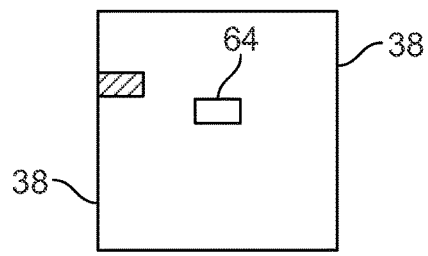
Figure 4I:
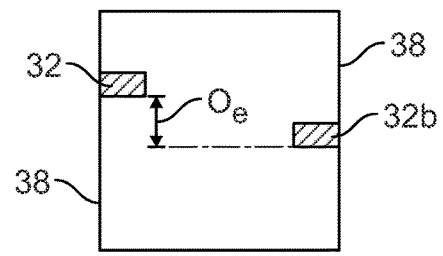
Figure 4J:
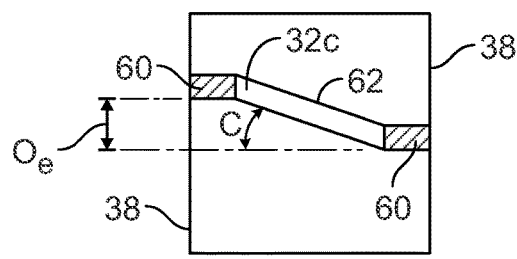

FIG. 4J is a cross-sectional view taken along line 4J-4J in FIG. 4E. The curved portion 62 of the raised edge 32 can define a plane that forms an angle (C) with a horizontal plane of the nail 10. The angle (C) can be substantially equal to the helix angle (A) of the fastener 26. The straight portions of the raised edge 32 positioned on parallel walls 38 of the slot 22 can be separated by an offset distance ($O_e$) in a direction generally parallel to the transverse axis 34 of the intramedullary nail 10.

A raised edge 32d can have top and bottom surfaces 46d, 48d that can be converging or tapered, and a leading edge 50d that can be sharp, as best seen in the cross-sectional view in FIG. 4G. The leading edge 50d can have a radius. An angle (D) formed between the top and bottom surfaces 46, 48 can be substantially equal to or less than the thread angle (B) of the fastener 26. Alternatively, the angle (D) can be larger than the thread angle (B).

FIG. 4K is a cross-sectional view taken along line 4K-4K in FIG. 4A. As shown in FIG. 4K, the groove 52 of the fastener 26 can engage the raised edge 32 such that the fastener 26 can slide axially relative to the nail 10 while being limited from sliding along the transverse axis 34. Because the fastener 26 is not angularly constrained by multiple blades positioned along the sidewall 38, as seen in the previous publications, that engage different portions of the groove 52, the fastener 26 can be tilted within the slot 22 such that fastener axes 34a, 34b can form, respectively, angles E, F with respect to the transverse axis 34.

Opposing sidewalls 38 can be substantially non-parallel to each other, for example converging as shown in FIG. 4L. Alternatively, or additionally, the opposing sidewalls 38 can be non-straight, including portions that are for example curved, jagged, or both. One or more raised edges 32e can be positioned on non-parallel and/or non-straight sidewalls such that the leading edge 50 of the raised edge 32e remains substantially straight and parallel to the longitudinal axis 28 of the implant 10, and the fastener 26 can translate along the longitudinal axis 28 while being prevented from sliding in a direction parallel to or along the transverse axis 34. Opposing sidewalls 38 can be joined by semi-cylindrical portions 40a, 40b.

FIG. 4M shows a cross-sectional view of an alternative raised edge configuration, where one or more, for example two, raised edges 32, 32f are positioned on one of the sidewalls 38 and arranged proximate each other in a direction substantially parallel to the transverse axis 34. Alternatively, one or more raised edges 32, 32f can be positioned on both of the opposing sidewalls 38. One or more raised edges 32, 32f are separate or disconnected elements such that they do not form a continuous surface between them.

Figure 5A:
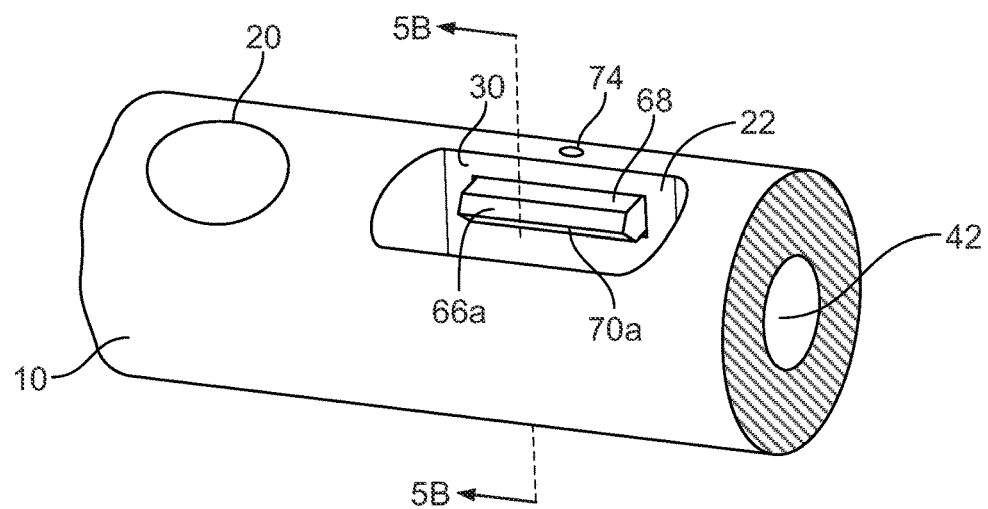
FIGS. 5A-5B are sectional perspective and cross-sectional views of a slot with a retractable edge.
Figure 5B:
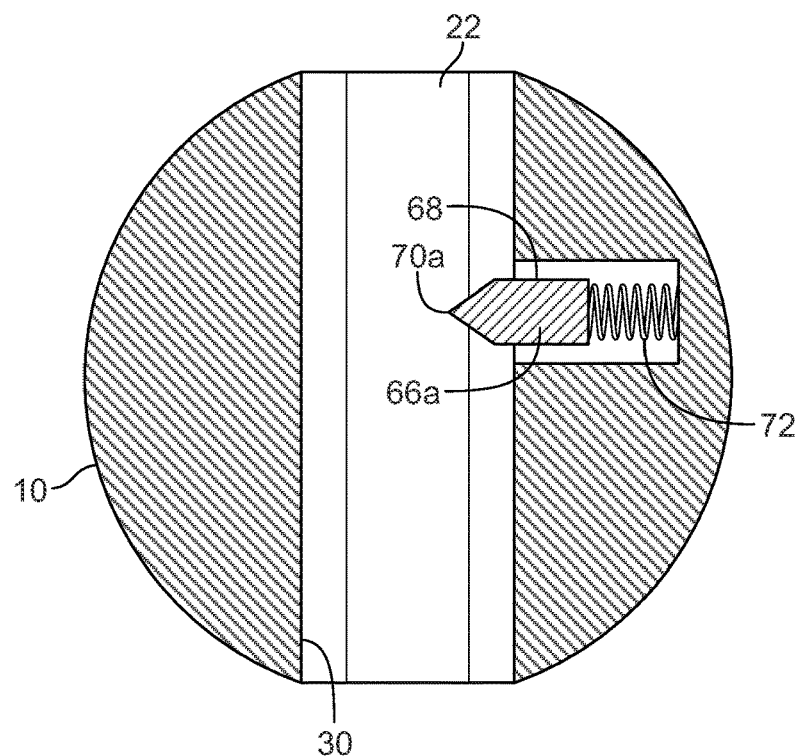

Referring to FIGS. 5A-5B, the inner wall 30 may be formed with a retractable edge 66a that engages the fastener 26 (not shown). The retractable edge 66a extends towards a longitudinal centerline of the slot 22 via an opening 68 formed in the inner wall 30 and can move along an axis that is substantially orthogonal to both the longitudinal axis 28 and the transverse axis 34. The retractable edge 66a includes a leading edge 70a that runs generally parallel to the longitudinal axis 28 of the intramedullary nail 10. The retractable edge 66a can be spring loaded with a spring 72 such that, absent an external force applied to the retractable edge 66a, the retractable edge 66a remains in a fully-deployed position with a maximally allowed portion of the retractable edge 66a extending into the slot 22. The retractable edge 66a can be pushed or retracted into the inner wall 30 upon exertion of an external force. For example, insertion of a fastener 26 into the slot 22 can cause the retractable edge 66a to correspondingly retract into the inner wall 30 due to engagement with, for example, the threads or groove 52 of the fastener 26. The spring 72 pushes against the retractable edge 32 to maintain contact between the fastener 26 and the retractable edge 32. A particular position of the retractable edge 32 with respect to the inner wall 30 can be locked using a set screw (not shown) inserted through a locking opening 74 or other suitable mechanisms.

Figure 6A:
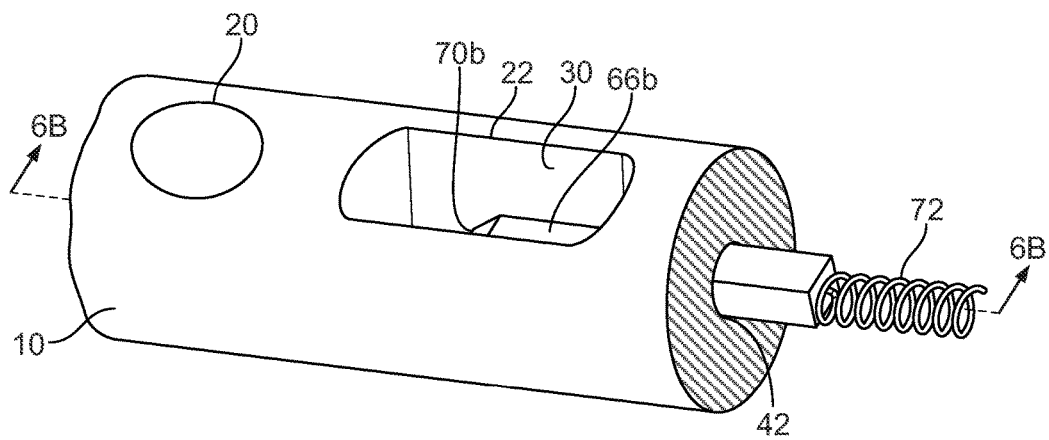
FIGS. 6A-6B are sectional perspective and partial cross-sectional views of an alternative slot with a retractable edge.
Figure 6B:
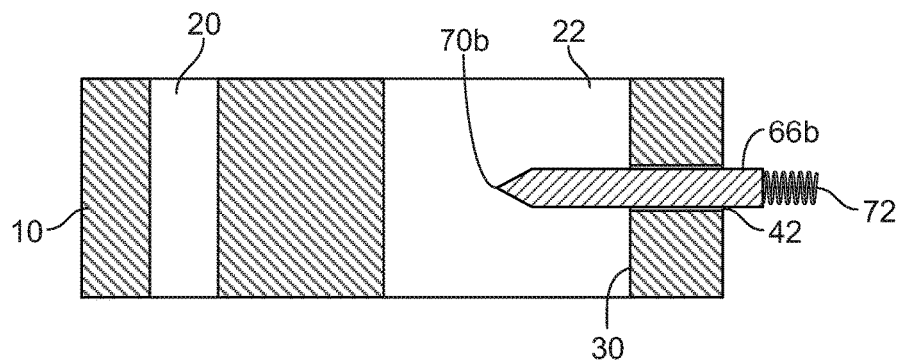
Figure 7A:
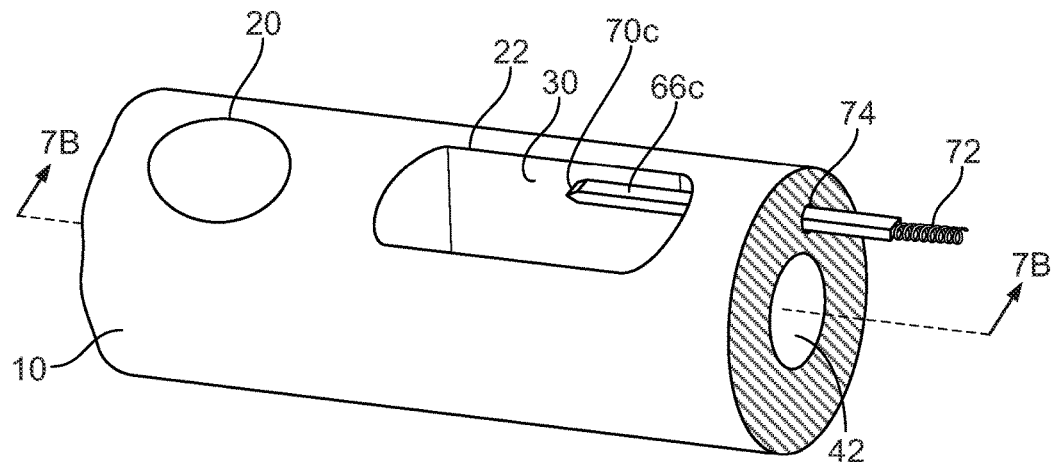
FIGS. 7A-7B are sectional perspective and partial cross-sectional views of another alternative slot with a retractable edge.
Figure 7B:
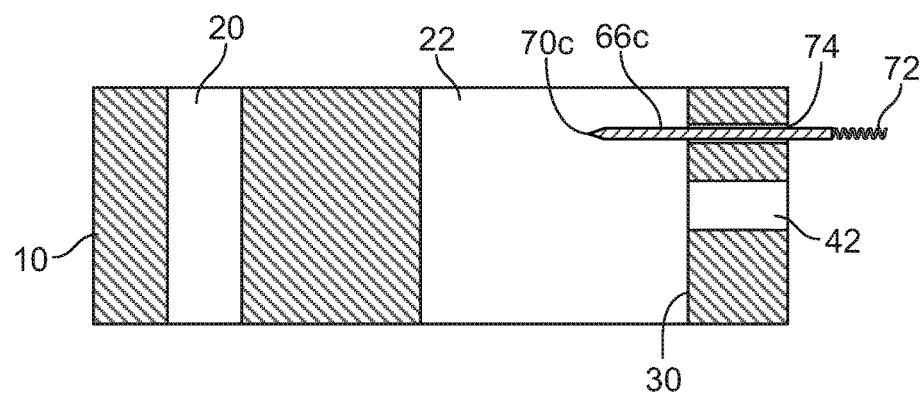
Figure 8A:
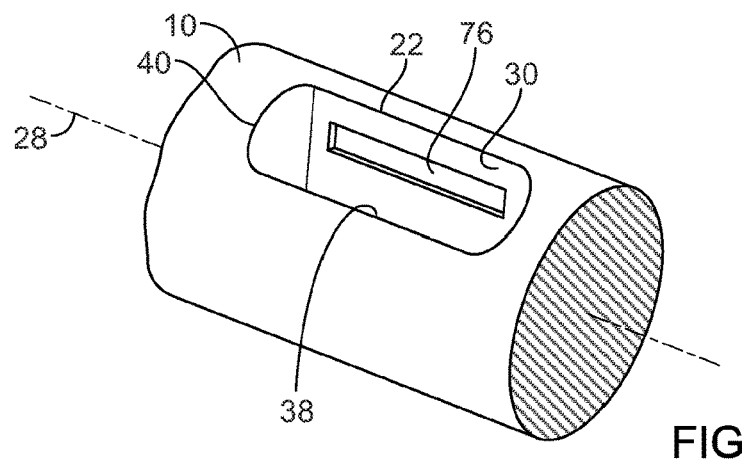
FIG. 8A is a sectional perspective view of an orthopaedic implant with a channel formed within a slot.
Figure 8B:
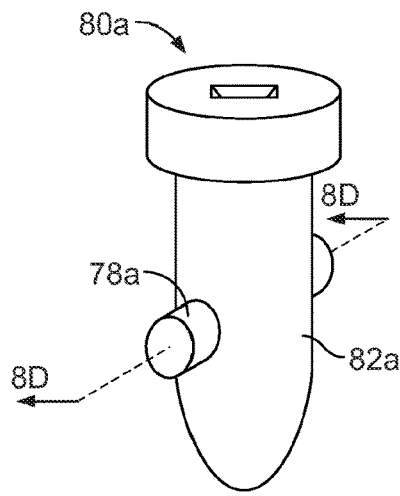
FIGS. 8B-8E are perspective and cross-sectional views of implementations of a fastener with a protrusion.
Figure 8C:
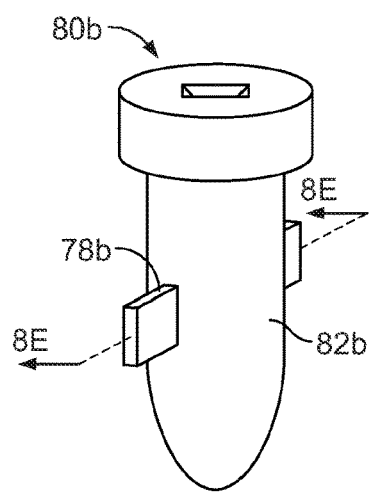
Figure 8D:
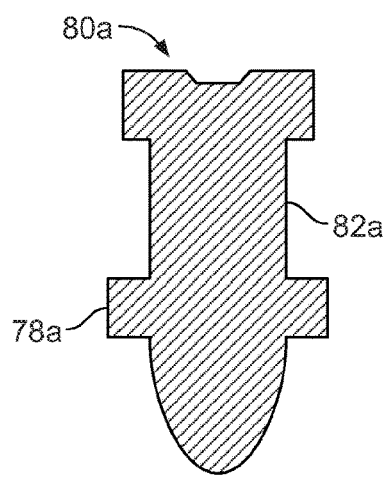
Figure 8E:
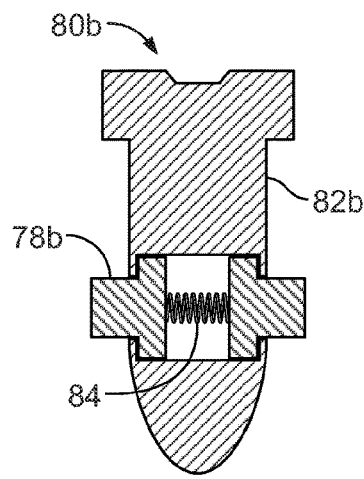

In another implementation, a retractable edge 66b can be positioned within the central cannulation 42 of the intramedullary nail 10, as shown in FIGS. 6A-6B. The central cannulation 42 creates an opening through the inner wall 30 into the slot 22 at a proximal and/or distal end of the slot 22. The retractable edge 66b can be inserted into the slot 22 through the proximal and/or distal end of the slot 22 and can be spring loaded with the spring 72 such that, absent an external force applied to the retractable edge 66b, the retractable edge 66b remains in a fully-deployed position with a maximally allowed portion of the retractable edge 66b extending into the slot 22. The retractable edge 66b can move along an axis that is substantially parallel to the longitudinal axis 28. The leading edge 70b of the retractable edge 66b can engage with the groove 52 of the fastener 26. In some cases, the retractable edge 66b can rotate with respect to its long axis within the cannulation 42 for improved engagement with the fastener 26. The spring 72 pushes against the retractable edge 66b to maintain contact between the fastener 26 and the retractable edge 66b. A particular position of the retractable edge 66b with respect to the inner wall 30 can be locked using, for example, a set screw (not shown). Additionally, the spring 72 can push against the retractable edge 66b to increase or decrease the force required for dynamization of, for example, the fracture site 14. Alternatively, a retractable edge 66c with a leading edge 70c can be positioned within an off-center cannulation 74 as best seen in FIGS. 7A-7B. Operation of the retractable edge 66c is similar to that described above with respect to the retractable edge 66c positioned within the cannulation 42 of the nail 10.

Referring to FIGS. 8A-8E, a depression, indentation, recess, or channel 76 elongated in a direction generally parallel to the longitudinal axis 28 can be formed in the inner wall 30 of the implant or nail 10. The channel 76 can be disposed on the opposing sidewalls 38 and/or the semi-cylindrical portion 40. The channel 76 can slidably engage with a protrusion 78a, 78b (FIGS. 8B-8E) of an inserted fastener 80a, 80b. Interaction between the channel 76 and the protrusion 78a, 78b of the fastener 80a, 80b limits sliding of the fastener 80a, 80b along an axis substantially transverse to the longitudinal axis 28 while allowing the fastener 80a, 80b to slide, or translate, along the longitudinal axis 28. One or more protrusions 78a, 78b of the fastener 80a, 80b extend radially outward beyond an outer surface of the body 82a, 82b. The protrusion 78a, 78b can include, but not limited to, shapes that are rectangular, pyramidal, cylindrical, spherical, wedge-shaped, or the like. The position of the protrusion 78a can be permanently fixed with respect to the body 82a of the fastener 80a, as illustrated in the cross-sectional view in FIG. 8D. Alternatively, as illustrated in the cross-sectional view in FIG. 8E, the one or more protrusions 78b can be moveably attached to the body 82b of the fastener 80b, such that the one or more protrusions 78b are expandable, deployable, and/or spring loaded with a spring 84. Additionally, the body 82a, 82b of the fastener 80a, 80b can include threads for securing to, for example, the cortical layer bone 24.

In use, for example, the fastener 80a can be inserted into the slot 22 by first rotationally orienting the fastener 80a around the transverse axis 34 such that the one or more protrusions 78a does not come in contact with the inner wall 30 of the nail 10 during insertion. For sliding engagement between the fastener 80a and the nail 10, the fastener 80a can be rotated, following insertion to a correct depth, around the transverse axis 34 until one or more protrusions 78a is inserted into the channel 76. Alternatively, or additionally, the one or more protrusions 78b can be expanded or deployed into the channel 76 following insertion of the fastener 80b into the slot 22.

Figure 9A:
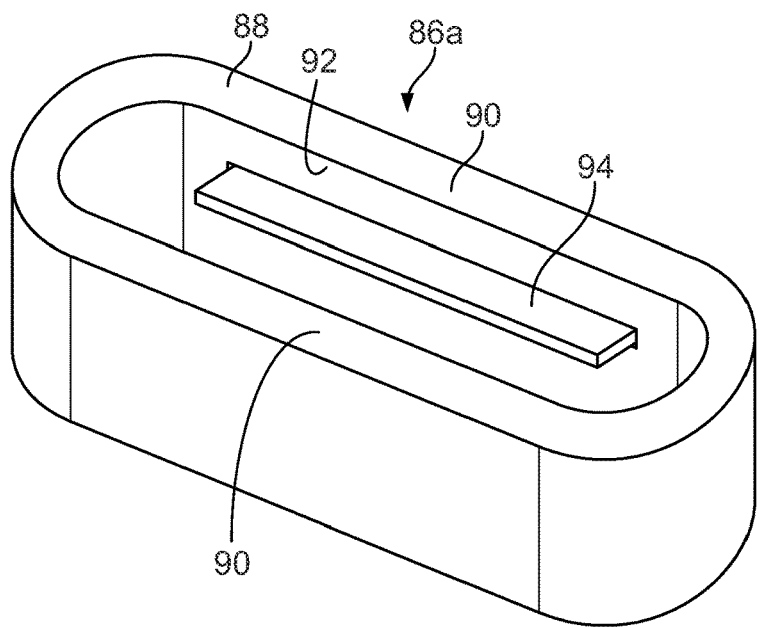
FIG. 9A is a perspective view of a slot insert with a raised edge.
Figure 9B:
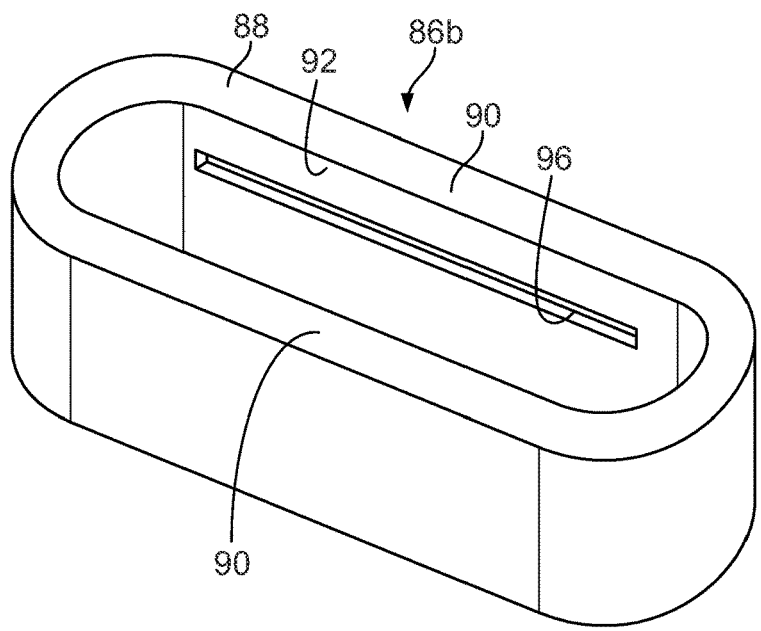
FIG. 9B is a perspective view of a slot insert with a channel.

Referring to FIGS. 9A-9B, a slot insert 86a, 86b can be inserted into an appropriately shaped opening in the orthopaedic implant, such as the intramedullary nail 10. Additionally, the slot insert 86a, 86b can be held in place within the appropriately shaped opening in the orthopaedic implant by welding, press-fit, one or more set screws, or other suitable attachment mechanisms. The slot insert 86a, 86b can be formed from any biocompatible material or a combination of biocompatible materials, such as certain metal alloys and polymers. The slot insert 86a, 86b includes an outer wall which has a shape mating whatever shape of a slot in the nail 10. The slot insert 86a, 86b includes a wall 88 that defines an open space within the slot insert 86 a, 86b that can include a pair of opposing or parallel walls 90. In use, the slot insert 86 is inserted into an appropriately shaped opening formed in, for example, the intramedullary nail 10 such that the pair of opposing or parallel walls 90 are positioned generally parallel to the longitudinal axis 28 of the nail 10. An inner surface 92 of the opposing or parallel walls 90 further defines a protrusion or raised edge 94 and/or a channel 96 as best seen, respectively, in FIGS. 9A and 9B. The fastener 26, 80 can be inserted into the insert 86 a, 86b such that the groove 52 and the protrusion 78, respectively, of the fastener 26, 80 slidably engages, respectively, the raised edge 94 and the channel 96 in the manners described above.

While this document contains many specific implementation details, these should not be construed as limitations on the scope of any implementations or of what may be claimed, but rather as descriptions of features specific to particular implementations of particular implementations. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Accordingly, other implementations are within the scope of the following claims.

What is claimed is:

1. An orthopaedic implant for use with a fastener, the implant comprising:
    a body defining a long axis, the body including an inner wall defining an elongated slot that extends through the body transverse to the long axis, the inner wall defining an opening therein, the inner wall comprising:
        a pair of opposing walls, and
        a single projection retractably disposed in the opening defined in the inner wall such that a portion of the single projection extends into the slot through the opening; wherein the pair of opposing walls face toward each other and run substantially parallel to the long axis, the pair of opposing walls defining at least a portion of the slot in a region between the opposing walls; and
    wherein, when the fastener is inserted into the slot, the single projection slidably fits within a groove of the fastener to limit sliding of the implant over the fastener along an axis substantially transverse to the long axis and to permit sliding of the body of the implant over the fastener along the long axis.

2. The orthopaedic implant of claim 1, wherein the body includes an outer wall, and the inner wall defines the elongated slot from an elongated opening at a first portion of the outer wall to an elongated opening at an opposed second portion of the outer wall.

3. The orthopaedic implant of claim 1, wherein the single projection disposed on the inner wall comprises a leading edge running substantially parallel to the long axis.

4. The orthopaedic implant of claim 1, further comprising a second single projection disposed on the inner wall, the second single projection having a leading edge running substantially parallel to the long axis and being positioned generally opposite the single projection.

5. The orthopaedic implant of claim 1, wherein the inner wall defines (i) a substantially cuboid portion of the slot between the pair of opposing walls and (ii) a semi-cylindrical portion of the slot.

6. The orthopaedic implant of claim 5, wherein the semi-cylindrical portion of the slot comprises an arc not greater than approximately 180 degrees.

7. The orthopaedic implant of claim 5, further comprising a projection disposed on the semi-cylindrical portion, the projection configured to engagingly fit within a groove of the fastener when the fastener is positioned proximate the projection disposed on the semi-cylindrical portion.

8. The orthopaedic implant of claim 7, wherein the projection disposed on the semi cylindrical portion forms a continuous surface with the single projection disposed on the inner wall.

9. The orthopaedic implant of claim 8, wherein the continuous surface runs circumferentially around the inner wall of the slot.

10. The orthopaedic implant of claim 1, wherein one or more additional projections are positioned on the inner wall such that the single projection and the one or more additional projections are aligned substantially parallel to the long axis, and wherein the one or more additional projections and the single projection are disconnected such that a continuous surface is not defined therebetween.

11. The orthopaedic implant of claim 1, wherein the pair of opposing walls are parallel to each other and spaced apart from each other a distance substantially corresponding to an outer diameter of the fastener.

12. The orthopaedic implant of claim 1, wherein the single projection is spring loaded.

13. The orthopaedic implant of claim 1, wherein the portion of the single projection extending into the slot can be lockably varied.

14. The orthopaedic implant of claim 1, wherein the single projection extends into the slot along an axis that is substantially parallel to the long axis or substantially orthogonal to the long axis.

15. The orthopaedic implant of claim 1, wherein the elongated slot is elongated along the long axis, and wherein the orthopaedic implant defines a cannula along the long axis.

16. The orthopaedic implant of claim 1, wherein the single projection is retractable out of the slot through the opening.

17. The orthopaedic implant of claim 1, wherein the elongated slot extends through the body substantially perpendicular to the long axis, and the elongated slot is elongated in the direction of the long axis.

18. The orthopaedic implant of claim 1, wherein the pair of opposing walls is a pair of substantially parallel walls that define a portion of the elongated slot; and
    wherein the substantially parallel walls extend along the long axis, and wherein the opening in which the single projection is retractably disposed is defined in one of the substantially parallel walls.

19. The orthopaedic implant of claim 1, wherein the single projection is configured to retract in a direction that is substantially orthogonal to the long axis.

20. The orthopaedic implant of claim 1, wherein the single projection is configured to retract in a direction that is substantially parallel to the long axis.

21. The orthopaedic implant of claim 1, wherein, when the fastener is inserted into the slot, the single projection slidably fits within a groove of the fastener to limit sliding of the implant over the fastener in both directions along the axis substantially transverse to the long axis.

22. The orthopaedic implant of claim 1, wherein, when the fastener is inserted into the slot, the single projection slidably fits within a groove of the fastener to permit sliding of the body of the implant over the fastener in both directions along the long axis.

23. The orthopaedic implant of claim 1, wherein the inner wall defines the elongated slot to extend along an axis, and wherein the opening in the inner wall is positioned such that the portion of the single projection extends into the elongated slot through the opening in a direction substantially perpendicular to the axis along which the elongated slot is defined.

24. A method of treating a bone fracture, comprising:
    inserting an orthopaedic implant into a canal of a fractured bone, the implant having a body defining a long axis, and an inner wall defining a hole and an elongated slot that extends through the body transverse to the long axis, the inner wall defining an opening therein; wherein the inner wall comprises a pair of opposing walls that face toward each other and run substantially parallel to the long axis, the pair of opposing walls defining at least a portion of the slot in a region between the opposing walls
    inserting a first fastener through the hole; and
    inserting a second fastener transversely through the slot of the implant;
    wherein the body of the implant is free to slide over the second fastener substantially along the long axis by interaction with at least a single projection disposed on the inner wall defining the slot, and with the second fastener in the slot the single projection slidably fits within a groove of the second fastener to limit sliding of the implant over the second fastener along an axis substantially transverse to the long axis, the projection having a leading edge running substantially parallel to the long axis, wherein the single projection is retractably disposed in the opening defined in the inner wall such that a portion of the single projection extends into the elongated slot through the opening, and wherein a first part of the fractured bone connected to the first fastener can move along the long axis in relation to a second part of the fractured bone connected to the second fastener.

25. An orthopaedic implant for use with a fastener, the implant comprising:
- a body defining a long axis, the body including an inner wall defining an elongated slot that extends through the body transverse to the long axis, the inner wall defining an opening therein, the inner wall comprising:
  - a pair of opposing walls, and
  - a projection disposed on the inner wall and having a leading edge parallel to the long axis, wherein the single projection is retractably disposed in the opening defined in the inner wall such that a portion of the single projection extends into the elongated slot through the opening;

wherein, when the fastener is inserted into the slot, at least a portion of the projection slidably fits within a groove of the fastener and establishes a point of contact with the fastener, the projection configured to limit sliding of the implant over the fastener along an axis substantially transverse to the long axis and to permit sliding of the body of the implant over the fastener along the long axis; and wherein the implant is arranged such that, as the body of implant slides over the fastener along the long axis, the point of contact with the fastener remains substantially the same.

26. The orthopaedic implant of claim 25, wherein the sliding of the implant over the fastener along the long axis does not cause the fastener to rotate.

27. The orthopaedic implant of claim 25, wherein when the fastener is at its final target depth within the implant, the implant can slide over the fastener along the long axis.

* * * * *